United States Patent
Truppo et al.

(10) Patent No.: US 9,523,107 B2
(45) Date of Patent: Dec. 20, 2016

(54) IMMOBILIZED TRANSAMINASES AND PROCESS FOR MAKING AND USING IMMOBILIZED TRANSAMINASE

(71) Applicant: Merck Sharp & Dohme Corp., Rahway, NJ (US)

(72) Inventors: Matthew D. Truppo, Bradley Beach, NJ (US); Michel Journet, Somerset, NJ (US); Hallena Strotman, Somerset, NJ (US); Jonathan P. McMullen, Jersey City, NJ (US); Shane T. Grosser, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/767,949

(22) PCT Filed: Feb. 24, 2014

(86) PCT No.: PCT/US2014/017898
§ 371 (c)(1),
(2) Date: Aug. 14, 2015

(87) PCT Pub. No.: WO2014/133928
PCT Pub. Date: Sep. 4, 2014

(65) Prior Publication Data
US 2015/0368682 A1  Dec. 24, 2015

Related U.S. Application Data

(60) Provisional application No. 61/770,366, filed on Feb. 28, 2013.

(51) Int. Cl.
| C12P 17/18 | (2006.01) |
| C12N 11/08 | (2006.01) |
| C12N 9/10 | (2006.01) |
| C12P 13/00 | (2006.01) |

(52) U.S. Cl.
CPC ........... *C12P 17/182* (2013.01); *C12N 9/1096* (2013.01); *C12N 11/08* (2013.01); *C12P 13/001* (2013.01); *Y02P 20/52* (2015.11)

(58) Field of Classification Search
None
See application file for complete search history.

(56) References Cited

U.S. PATENT DOCUMENTS

| 7,326,708 B2 | 2/2008 | Cypes et al. |
| 7,468,459 B2 | 12/2008 | Xiao et al. |
| 8,293,507 B2 | 10/2012 | Savile et al. |
| 2010/0285541 A1 | 11/2010 | Saville et al. |
| 2011/0033391 A1 | 2/2011 | Weiner |
| 2016/0002688 A1* | 1/2016 | Quintanar-Audelo C12N 9/1096 435/119 |

FOREIGN PATENT DOCUMENTS

| WO | WO03068909 A2 | 8/2003 |
| WO | WO2004085624 A2 | 10/2004 |
| WO | WO2007133184 A2 | 11/2007 |
| WO | WO2011005477 A1 | 1/2011 |
| WO | WO2012177527 A1 | 12/2012 |

OTHER PUBLICATIONS

Database Geneseq, "*Arthrobacter* sp. KNK168 variant transaminase SEQ: 160.", retrieved from EBI, accession No. GSP:AYN58117 2016.
Brena, B. M. et al, Immobilization of Enzymes, Methods in Biotechnology: Immobilization of Enzymes and Cells, 2006, p. 15-30.
Devine, H. G. et al., *Arthrobacter* sp. KNK168 variant transaminase SEQ:110, Database Geneseq, 2011, p. 1-2.
Hernandez, K. et al., Lipase B from Candida antarctica immobilized on octadecyl Sepabeads: A very stable biocatalyst in the presence of hydrogen peroxide, Process Biochemistry, 2011, p. 873-878, vol. 46.
Hilterhaus, L. et al, Practical application of different enzymes immobilized on sepabeads, Bioprocess Biosyst Eng, 2008, p. 163-171, vol. 31.
Iwasaki, A, et al., A novel transaminase, (R)-amine:pyruvate aminotransferase, from *Arthrobacter* sp. KNK168 (FERM BP-5228): purification, characterization, and gene cloning, Appl Microbiol Biotechnol, 2012, p. 163-1573, 93.
Knezevic-Jugovic, Z. D. et al., The Immobilization of Lipase on Sepabeads: Coupling, Characterization and Application in Geranyl Butyrate Synthesis in a Low Aqueous System, Chemical Industry & Chemical Engineering Quarterly, 2008, p. 245-249, vol. 14, No. 4.
Martin, A. R. et al., Characterization of free and immobilized (S)-aminotransferase for acetophenone production, Appl Microbiol Biotechnol, 2007, p. 843-851, vol. 76.
Mitsubishi Chemical Corporation, Diaion, Product Line Brochure, 2011, p. 17, 0.
Savile, C. K. et al., Biocatalytic Asymmetric Synthesis of Chiral Amines from Ketones Applied to Sitagliptin Manufacture, Science, 2010, p. 305-, vol. 329.
Song-Se Yi, et al, Covalent immobilization of w-transaminase from Vibrio fluvialis JS17 on chitosan beads, Process Biochemistry, 2007, p. 895-898, 42.
Sun, J. et al., Immobilization of Candida antarctica lipase B by adsorption in organic medium, New Biotechnology, 2010, p. 53-, vol. 27, No. 1.
Truppo, M. D. et al, Development of an Immobilized Transaminase Capable of Operating in Organic Solvent, ChemCatChem, 2012, p. 1071-1074, vol. 4, No. 8.
Truppo, M. D. et al., Efficient kinetic resolution of racemic amines using a transaminase in combination with an amino acid oxidase, Chem. Commun, 2009, p. 2127-2129, 0.
Truppo, M. D. Eta L., Efficient Production of Enantiomerically Pure Chiral Amines at Concentrations of 50 g/L Using Transaminases, Organic Process Research & Development, 2010, p. 234-237, vol. 14.
Turner, N. J. et al., Chiral Amine Synthesis: Methods, Developments and Applications, Biocatalytic Routes to Nonracemic Chiral Amines, 2010, p. 441-455, 0.

\* cited by examiner

*Primary Examiner* — David J Steadman
(74) *Attorney, Agent, or Firm* — Janet E. Fair; Anna L. Cocuzzo

(57) ABSTRACT

The invention is directed to immobilized transaminases and methods of making and using them.

11 Claims, No Drawings

IMMOBILIZED TRANSAMINASES AND PROCESS FOR MAKING AND USING IMMOBILIZED TRANSAMINASE

CROSS-REFERENCE TO RELATED APPLICATIONS

This application is a U.S. National Phase application under 35 U.S.C. §371 of PCT Application No. PCT/US2014/017898, filed Feb. 24, 2014, which published as WO 2014/133928A1 on Sep. 4, 2014, and claims priority under 35 U.S.C. §365(b) from U.S. provisional patent application No. 61/770,366, filed Feb. 28, 2013.

TECHNICAL FIELD OF THE INVENTION

The invention is directed to immobilized transaminases and methods of making and using them.

REFERENCE TO SEQUENCE LISTING, TABLE OR COMPUTER PROGRAM

The official copy of the Sequence Listing is submitted concurrently with the specification as an ASCII formatted text file via EFS-Web, with a file name of "23277-US-PSP.txt", a creation date of Feb. 26, 2013 and a size of 8,192 bytes. The Sequence Listing filed via EFS-Web is part of the specification and incorporated in its entirety by reference herein.

BACKGROUND OF THE INVENTION

Enzymes are protein molecules which serve to accelerate the chemical reactions of living cells (often by several orders of magnitude). Without enzymes, most biochemical reactions would be too slow to even carry out life processes. Enzymes display great specificity and are not permanently modified by their participation in reactions. Since they are not changed during the reactions, enzymes can be cost effectively used as catalysts for a desired chemical transformation.

Transaminases are a specific class of enzymes that catalyze the direct amination of ketones to chiral amines. Enantiomerically pure chiral amines are key intermediates in the synthesizing of a number of pharmaceutical compounds that possess a wide range of biological activities. Currently there is considerable effort underway to develop efficient catalytic methods for their preparation utilizing biocatalysts. Recently transaminases have emerged as promising biocatalysts for chiral amine production. Truppo et al., *Efficient kinetic resolution of recemic amines using a transaminase in combination with an amino acid oxidase*, Chem. Commun., 2009, 2127-2129; and Truppo et al., *Efficient Production of Enantiomerically Pure Chiral Amines at Concentrations of 50 g/L Using Transaminases*, Organic Process Research & Development 2010, 14, 234-237.

For example, rhodium-catalized asymmetric enamine hydrogenation was originally used for the large-scale manufacture of the antidiabetic compound sitagliptin. The rhodium was replaced with a tranaminase which ultimately has lead to an enzymatic process that reduces waste, improves yield and safety, and eliminates the need for a metal catalyst. Moreover, the resultant biocatalyst showed broad applicability toward the synthesis of chiral amines that previously were accessible only via resolution. Savile et al., *Biocatalytic Asymmetric Synthesis of Chiral Amines from Ketones Applied to Sitagliptin Manufacture*, Science, Vol. 329, pgs. 305-309, 16 Jul. 2010.

Though advances in producing chiral amines using transaminases have been highly regarded, there still exits some drawbacks to the enzymatic process. Currently enzymatic processes can only be run in aqueous solvent systems as the transaminases are not stable in 100% organic solvents. Additionally, during product amine isolation, the transaminase catalyst is deactivated and discarded resulting in the inability to reuse the catalyst.

Thus, though attempts have been made to immobilize transaminases none have been successful in overcoming their lack of stability, more specifically their lack of stability in organic solvents.

SUMMARY OF THE INVENTION

Described herein, are immobilized transaminases comprising a recombinant transaminase physically attached to a resin. The immobilized transaminases described herein include recombinant transaminases that are capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels measurable by an analysis technique. In certain embodiments the immobilized transaminases described herein are used to make (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

In certain embodiments, described herein are immobilized transaminases comprising a recombinant transaminase that is capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels measurable by an analysis technique; and a resin, wherein the recombinant transaminase is attached to the resin by physical interactions, and wherein the immobilized transaminase is stable in a solvent system that comprises at least 90% of organic solvents.

For example in one embodiment, the recombinant transaminase is attached to a resin by hydrophilic interactions.

The immobilized transaminases described herein are stable in organic solvents systems. As used herein stable immobilized transaminases mean that the immobilized transaminase retains its structural conformation or its activity, in organic solvent systems. In one embodiment described herein, the immobilized transaminase is stable in a solvent system that comprises at least 95% of organic solvents.

In certain embodiments described herein, the recombinant transaminase is a transaminase that is capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels measurable by HPLC-UV absorbance.

In yet another embodiment the recombinant transaminase is selected from the group consisting of: SEQ ID NO: 1.

In certain embodiments of the immobilized transaminases described herein, the resin comprises methacrylates. For example in one embodiment, the resin is synthesized from methacrylates, wherein the monomer and the crosslinker are methacrylates. In certain embodiments, the resin does not contain any aromatic compounds. In other embodiments, the resin is DIAION HP2MG (Mistubishi). DIAION HP2MG is a high porous, methacrylate based adsorption resin which is synthesized only from methacrylates (monomer and crosslinker are methacrylates). DIAION HP2MG (Mistubishi) does not contain any aromatic compounds, and is considered an intermediate polarity adsorption resin. DIAION HP2MG (Mistubishi) is suitable for desalting and adsorption of organic compounds of relatively high polarity by using the more hydrophilic characteristics of the polymer matrix.

In one embodiment, of the immobilized transaminase, transaminase SEQ ID NO: 1 is attached to the resin DIAION HP2MG (Mitsubishi). In another embodiment, the transaminase SEQ ID NO: 1 is attached to the resin DIAION HP2MG (Mitsubishi) via hydrophilic interactions.

Also, described herein are methods of making and using the immobilized transaminases. The immobilized transaminases described herein can be used in batch reactions, wherein the immobilized transaminases can be filtered out after the reaction is complete and reused in other reactions. Alternatively, the immobilized transaminases described herein can be used in a continuous reaction system wherein the starting material is continuously passed over the immobilized transaminase and the product is collected.

In one embodiment the process described herein is a process for making (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprising the steps of:

1) dissolving 4-oxo-4-[3-(trifluoromethyl)-5,6-dihydro[1,2,4]triazolo[4,3-a]pyrazin-7(8H)-yl]-1-(2,4,5-trifluorophenyl)butan-2-one in an organic solvent;

2) contacting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an immobilized transaminase that is capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in presence of an amino group.

Preferably in such a process the immobilized transaminase is the transaminase SEQ ID NO: 1 physically attached to the resin DIAION (Mitsubishi).

Also described herein is a process of making an immobilized transaminase comprising:

1) incubating a solution of tranaminase with a resin and an enzyme solution to form an immobilized transaminase;

2) filtering and rinsing the immobilized transaminase;

3) drying the immobilized transaminase.

DETAILED DESCRIPTION OF THE INVENTION

Definitions

"Transaminase", also called "aminotransferase", is used herein to refer to a polypeptide having an enzymatic capability of transferring an amino group ($NH_2$) and a hydrogen atom from a primary amine (3) to an acceptor carbonyl compound (2), converting the amine donor into its corresponding carbonyl compound (4) and the acceptor into its corresponding primary amine (1):

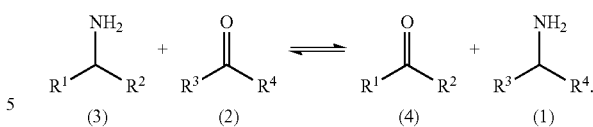

With regard to the immobilized transaminases described herein, the transaminase polypeptides are capable of converting the substrate of formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one (the "ketoamide substrate"), to the product of formula (1a) (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (the "product) in presence of an amino group donor of formula (3), as follows:

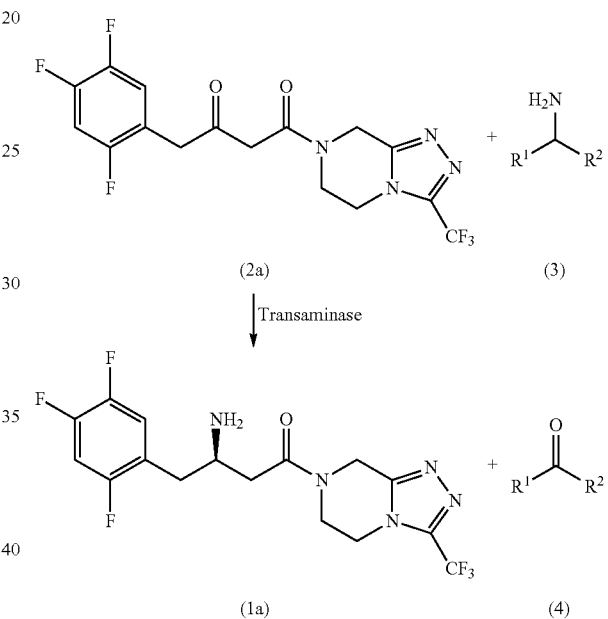

wherein each of $R^1$, $R^2$, $R^3$ and $R^4$ when taken independently, is an alkyl, an alkylaryl group, or aryl group which is unsubstituted or substituted with one or more enzymatically non-inhibiting groups. $R^1$ and $R^3$ can be the same or different from $R^2$ and $R^4$ respectively in structure or chirality. The groups $R^1$ and $R^2$ or $R^3$ and $R^4$, taken together, may form a ring that is unsubstituted, substituted, or fused to other rings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.). Included within this definition are D- and L-amino acids, and mixtures of D- and L-amino acids.

"Substrate" as used herein refers to an amino group acceptor, such as a ketone, that accepts the amino group from an amino group donor in a reaction mediated by a transaminase. Substrates can include the compound of formula (II), the compound of formula (2) and the compound of formula (2a), as further described herein. In certain processes described herein, "ketoamide substrate" specifically refers to the compound of formula (2a), 4-oxo-4-[3-

(trifluoromethyl)-5,6-dihydro[1,2,4]triazolo[4,3-a]pyrazin-7(8H)-yl]-1-(2,4,5-trifluorophenyl)butan-2-one.

"Amino group donor" refers to an amino compound which is capable of donating an amino group to an acceptor carbonyl compound (i.e., an amino group acceptor), thereby becoming a carbonyl by-product Amino group donors are molecules of general formula (3),

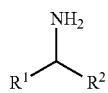

(3)

in which each of $R^1$, $R^2$, when taken independently, is an alkyl, an alkylaryl group, or aryl group which is unsubstituted or substituted with one or more enzymatically non-inhibiting groups. $R^1$ can be the same or different from $R^2$ in structure or chirality. The groups $R^1$ and $R^2$, taken together, may form a ring that is unsubstituted, substituted, or fused to other rings. Typical amino group donors that can be used with the invention include chiral and achiral amino acids, and chiral and achiral amines.

"Chiral amine" refers to amines of general formula $R^1$—$CH(NH_2)$—$R^2$ wherein $R^1$ and $R^2$ are nonidentical and is employed herein in its broadest sense, including a wide variety of aliphatic and alicyclic compounds of different, and mixed, functional types, characterized by the presence of a primary amino group bound to a secondary carbon atom which, in addition to a hydrogen atom, carries either (i) a divalent group forming a chiral cyclic structure, or (ii) two substituents (other than hydrogen) differing from each other in structure or chirality. Divalent groups forming a chiral cyclic structure include, for example, 2-methylbutane-1,4-diyl, pentane-1,4-diyl, hexane-1,4-diyl, hexane-1,5-diyl, 2-methylpentane-1,5-diyl. The two different substituents on the secondary carbon atom ($R_1$ and $R_2$ above) also can vary widely and include alkyl, aralkyl, aryl, halo, hydroxy, lower alkyl, lower alkoxy, lower alkylthio, cycloalkyl, carboxy, carboalkoxy, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc., as well as alkyl, aralkyl, or aryl substituted by the foregoing.

"Carbonyl by-product" refers to the carbonyl compound formed from the amino group donor when the amino group on the amino group donor is transferred to the amino group acceptor in a transamination reaction. The carbonyl by-product has the general structure of formula (4):

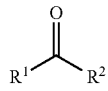

(4)

wherein $R_1$ and $R_2$ are defined above for the amino group donor.

"Pyridoxal-phosphate", "PLP", "pyridoxal-5'-phosphate", "PYP", and "P5P" are used interchangeably herein to refer to the compound that acts as a coenzyme in transaminase reactions. In some embodiments, pyridoxal phosphate is defined by the structure 1-(4'-formyl-3'-hydroxy-2'-methyl-5'-pyridyl)methoxyphosphonic acid, CAS number [54-47-7]. Pyridoxal-5'-phosphate is produced in vivo by phosphorylation and oxidation of pyridoxol (also known as pyridoxine or Vitamin B6). In transamination reactions using transaminase enzymes, the amino group of the amino group donor is transferred to the coenzyme to produce a keto byproduct, while pyridoxal-5'-phosphate is converted to pyridoxamine phosphate. Pyridoxal-5'-phosphate is regenerated by reaction with a different keto compound (the amino group acceptor). The transfer of the amino group from pyridoxamine phosphate to the amino acceptor produces a chiral amine and regenerates the coenzyme. The pyridoxal-5'-phosphate of the current invention can be replaced by other members of the vitamin B6 family, including, among others, pyridoxal (PL), pyridoxamine (PM), and their phosphorylated counterparts; pyridoxine phosphate (PNP), and pyridoxamine phosphate (PMP).

"Naturally occurring" or "wild-type" refers to a form found in nature. For example, a naturally occurring or wild-type polypeptide or polynucleotide sequence is a sequence present in an organism that can be isolated from a source in nature and which has not been intentionally modified by human manipulation.

"Recombinant" when used with reference to, e.g., a cell, nucleic acid, or polypeptide, refers to a material, or a material corresponding to the natural or native form of the material, that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Percentage of sequence identity," "percent identity," and "percent identical" are used herein to refer to comparisons between polynucleotide sequences or polypeptide sequences, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage is calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Determination of optimal alignment and percent sequence identity is performed using the BLAST and BLAST 2.0 algorithms (see e.g., Altschul et al., 1990, J. Mol. Biol. 215: 403-410 and Altschul et al., 1977, Nucleic Acids Res. 3389-3402). Software for performing BLAST analyses is publicly available through the National Center for Biotechnology Information website.

Briefly, the BLAST analyses involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff, 1989, Proc Natl Acad Sci USA 89:10915).

Numerous other algorithms are available that function similarly to BLAST in providing percent identity for two sequences. Optimal alignment of sequences for comparison can be conducted, e.g., by the local homology algorithm of Smith and Waterman, 1981, Adv. Appl. Math. 2:482, by the homology alignment algorithm of Needleman and Wunsch, 1970, J. Mol. Biol. 48:443, by the search for similarity method of Pearson and Lipman, 1988, Proc. Natl. Acad. Sci. USA 85:2444, by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)). Additionally, determination of sequence alignment and percent sequence identity can employ the BESTFIT or GAP programs in the GCG Wisconsin Software package (Accelrys, Madison Wis.), using default parameters provided.

"Substantial identity" refers to a polynucleotide or polypeptide sequence that has at least 80 percent sequence identity, preferably at least 85 percent sequence identity, more preferably at least 89 percent sequence identity, more preferably at least 95 percent sequence identity, and even more preferably at least 99 percent sequence identity as compared to a reference sequence over a comparison window of at least 20 residue positions, frequently over a window of at least 30-50 residues, wherein the percentage of sequence identity is calculated by comparing the reference sequence to a sequence that includes deletions or additions which total 20 percent or less of the reference sequence over the window of comparison. In specific embodiments applied to polypeptides, the term "substantial identity" means that two polypeptide sequences, when optimally aligned, such as by the programs GAP or BESTFIT using default gap weights, share at least 80 percent sequence identity, preferably at least 89 percent sequence identity, more preferably at least 95 percent sequence identity or more (e.g., 99 percent sequence identity). Preferably, residue positions which are not identical differ by conservative amino acid substitutions.

"Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity, the fraction (typically reported as a percentage) of one enantiomer in the sum of both. It is commonly alternatively reported in the art (typically as a percentage) as the enantiomeric excess (e.e.) calculated therefrom according to the formula [major enantiomer−minor enantiomer]/[major enantiomer+minor enantiomer]. Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

"Highly stereoselective" refers to a chemical or enzymatic reaction that is capable of converting a substrate (e.g., formula (2a)) to its corresponding product (e.g., formula (1a)) with at least about 85% stereoisomeric excess.

"Conversion" refers to the enzymatic transformation of a substrate to the corresponding product. "Percent conversion" refers to the percent of the substrate that is converted to the product within a period of time under specified conditions. Thus, for example, the "enzymatic activity" or "activity" of a transaminase polypeptide can be expressed as "percent conversion" of the substrate to the product.

"Stable" refers to the ability of the immobilized enzymes described herein to retain their structural conformation and/or their activity in a solvent system that contains organic solvents. In certain embodiments, stable immobilized enzymes lose less than 10% activity per hour in a solvent system that contains organic solvents. Preferably, the stable immobilized enzymes described herein less than 9% activity per hour in a solvent system that contains organic solvents. Preferably, the stable immobilized enzymes described herein less than 8% activity per hour in a solvent system that contains organic solvents. Preferably, the stable immobilized enzymes described herein less than 7% activity per hour in a solvent system that contains organic solvents. Preferably, the stable immobilized enzymes described herein less than 6% activity per hour in a solvent system that contains organic solvents. Preferably, the stable immobilized enzymes described herein less than 5% activity per hour in a solvent system that contains organic solvents. Preferably, the stable immobilized enzymes described herein less than 4% activity per hour in a solvent system that contains organic solvents. Preferably, the stable immobilized enzymes described herein less than 3% activity per hour in a solvent system that contains organic solvents. Preferably, the stable immobilized enzymes described herein less than 2% activity per hour in a solvent system that contains organic solvents. Preferably, the stable immobilized enzymes described herein less than 1% activity per hour in a solvent system that contains organic solvents.

"Amino acid" or "residue" as used in context of the polypeptides disclosed herein refers to the specific monomer at a sequence position.

"Hydrophilic amino acid or residue" refers to an amino acid or residue having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include L-Thr (T), L Ser (S), L His (H), L Glu (E), L Asn (N), L Gln (Q), L Asp (D), L Lys (K) and L Arg (R).

"Acidic amino acid or residue" refers to a hydrophilic amino acid or residue having a side chain exhibiting a pK value of less than about 6 when the amino acid is included in a peptide or polypeptide. Acidic amino acids typically have negatively charged side chains at physiological pH due to loss of a hydrogen ion. Genetically encoded acidic amino acids include L Glu (E) and L Asp (D).

"Basic amino acid or residue" refers to a hydrophilic amino acid or residue having a side chain exhibiting a pKa value of greater than about 6 when the amino acid is included in a peptide or polypeptide. Basic amino acids typically have positively charged side chains at physiological pH due to association with hydronium ion. Genetically encoded basic amino acids include L Arg (R) and L Lys (K).

"Polar amino acid or residue" refers to a hydrophilic amino acid or residue having a side chain that is uncharged at physiological pH, but which has at least one bond in which the pair of electrons shared in common by two atoms is held more closely by one of the atoms. Genetically encoded polar amino acids include L Asn (N), L Gln (Q), L Ser (S) and L Thr (T).

"Hydrophobic amino acid or residue" refers to an amino acid or residue having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include L Pro (P), L Ile (I), L Phe (F), L Val (V), L Leu (L), L Trp (W), L Met (M), L Ala (A) and L Tyr (Y).

"Aromatic amino acid or residue" refers to a hydrophilic or hydrophobic amino acid or residue having a side chain that includes at least one aromatic or heteroaromatic ring. Genetically encoded aromatic amino acids include L Phe (F), L Tyr (Y), L His (H) and L Trp (W). L His (H) histidine is classified herein as a hydrophilic residue or as a constrained residue.

"Non-polar amino acid or residue" refers to a hydrophobic amino acid or residue having a side chain that is uncharged at physiological pH and which has bonds in which the pair of electrons shared in common by two atoms is generally held equally by each of the two atoms (i.e., the side chain is not polar). Genetically encoded non-polar amino acids include L Gly (G), L Leu (L), L Val (V), L Ile (I), L Met (M) and L Ala (A).

"Aliphatic amino acid or residue" refers to a hydrophobic amino acid or residue having an aliphatic hydrocarbon side chain. Genetically encoded aliphatic amino acids include L Ala (A), L Val (V), L Leu (L) and L Ile (I).

"Cysteine" or L Cys (C) is unusual in that it can form disulfide bridges with other L Cys (C) amino acids or other sulfanyl- or sulfhydryl-containing amino acids. The "cysteine-like residues" include cysteine and other amino acids that contain sulfhydryl moieties that are available for formation of disulfide bridges. The ability of L Cys (C) (and other amino acids with SH containing side chains) to exist in a peptide in either the reduced free SH or oxidized disulfide-bridged form affects whether L Cys (C) contributes net hydrophobic or hydrophilic character to a peptide. While L Cys (C) exhibits a hydrophobicity of 0.29 according to the normalized consensus scale of Eisenberg (Eisenberg et al., 1984, supra), it is to be understood that for purposes of the present disclosure L Cys (C) is categorized into its own unique group.

"Hydroxyl-containing amino acid or residue" refers to an amino acid containing a hydroxyl (—OH) moiety. Genetically-encoded hydroxyl-containing amino acids include L Ser (S) L Thr (T) and L-Tyr (Y).

Transaminases

In general, transaminases catalyze the direct amination of ketones to chiral amines. Examples of transaminases include any polypeptide having an enzymatic capability of transferring an amino group ($NH_2$) and a hydrogen atom from a primary amine (3) to an acceptor carbonyl compound (2), converting the amine donor into its corresponding carbonyl compound (4) and the acceptor into its corresponding primary amine (1):

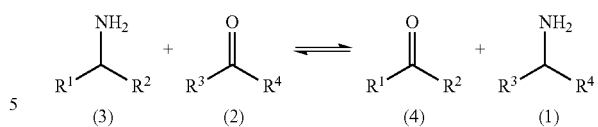

wherein each of $R^1$, $R^2$, $R^3$ and $R^4$ when taken independently, is an alkyl, an alkylaryl group, or aryl group which is unsubstituted or substituted with one or more enzymatically non-inhibiting groups. $R^1$ and $R^3$ can be the same or different from $R^2$ and $R^4$ respectively in structure or chirality. The groups $R^1$ and $R^2$ or $R^3$ and $R^4$, taken together, may form a ring that is unsubstituted, substituted, or fused to other rings.

Described herein are immobilized transaminases comprising recombinant transaminases that are capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one ("the ketoamide substrate") to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ("the product").

In certain embodiments of the immobilized transaminases described herein, the immobilized transaminases include transaminases that are capable of converting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one ("the ketoamide substrate") to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ("the product") in the presence of an amino group donor to levels measurable by an analysis technique, such as HPLC-UV absorbance.

In other embodiments of the immobilized transaminases described herein, the immobilized transaminases include transaminases of SEQ ID NO: 1.

In still yet other embodiments of the immobilized transaminases described herein, the immobilized transaminases include transaminases that are capable of improving conversion of 4-oxo-4-[3-(trifluoromethyl)-5,6-dihydro[1,2,4]triazolo[4,3-a]pyrazin-7(8H)-yl]-1-(2,4,5-trifluorophenyl)butan-2-one ("the ketoamide substrate") to (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ("the product"), as compared to such transaminases described in US Patent Publication No. 2010/0285541, filed Feb. 26, 2010, which is incorporated herein in its entirety by reference, in the presence of an amino group donor to levels measurable by an analysis technique, such as HPLC-UV absorbance.

In some embodiments, transaminases capable of converting the ketoamide substrate, 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in the presence of an amino group donor to levels of product detectable by an analysis technique, such as HPLC-UV absorbance comprise an amino acid sequence corresponding to the sequence of SEQ ID NO: 1.

In some embodiments, the transaminases comprise an amino acid sequence that is at least about 80%, 85%, 86%, 87%, 88%, 89%, 90%, 91%, 92%, 93%, 94%, 95%, 96%, 97%, 98%, or 99% identical to a reference sequence of SEQ ID NO: 1.

In certain embodiments of the immobilized transaminases described herein, the transaminase is selected from the group consisting of: SEQ ID NO: 1.

The immobilized transaminases described herein include a transaminase that is physically attached to a solid support by physical interactions, such as hydrophilic interactions.

In certain embodiments of the immobilized transaminases described herein, the immobilized transaminases include a transaminase that is physically attached to a solid support. Suitable transaminases include acidic or basic amino acids or residues. Acidic amino acids include L Glu (E) and L Asp (D). Basic amino acids include L Arg (R) and L Lys (K). Other transaminases that can be physically attached to a solid support include transaminases that include hydrophilic amino acids or residues, hydroxyl-containing amino acids or residues or polar amino acids or residues or transaminases, such as Arg (R), Lys (K), His (H), Asn (N) and Pro (P). In certain embodiments, the transaminases can include non-polar amino acids or residues such as, but not limited to L Gly (G), L Leu (L), L Val (V), L Ile (I), L Met (M) and L Ala (A). In other embodiments, the transaminases can include aliphatic amino acids or residues such as, but not limited to L Ala (A), L Val (V), L Leu (L) and L Ile (I). In still other embodiments, the transaminases can include aromatic amino acids or residues such as, but not limited to, Arg (R), Lys (K), His (H), Asn (N) and Pro (P).

A suitable example of a transaminase that is physically attached to a solid support, such as a resin, is SEQ ID NO: 1. A suitable example of a transaminase that is physically attached to a solid support, such as a resin, by hydrophilic interactions is SEQ ID NO: 1.

As described herein, the transaminase polypeptides of the disclosure can be in the form of fusion polypeptides in which the transaminase polypeptides are fused to other polypeptides, such as, by way of example and not limitation, antibody tags (e.g., myc epitope), purifications sequences (e.g., His tags for binding to metals), and cell localization signals (e.g., secretion signals). Thus, the transaminase polypeptides can be used with or without fusions to other polypeptides.

The polypeptides described herein are not restricted to the genetically encoded amino acids. In addition to the genetically encoded amino acids, the polypeptides described herein may be comprised, either in whole or in part, of naturally-occurring and/or synthetic non-encoded amino acids. Certain commonly encountered non-encoded amino acids of which the polypeptides described herein may be comprised include, but are not limited to: the D-stereoisomers of the genetically-encoded amino acids; 2,3-diaminopropionic acid (Dpr); a aminoisobutyric acid (Aib); e amino-hexanoic acid (Aha); δ aminovaleric acid (Ava); N-methylglycine or sarcosine (MeGly or Sar); ornithine (Orn); citrulline (Cit); t-butylalanine (Bua); t-butylglycine (Bug); N-methylisoleucine (MeIle); phenylglycine (Phg); cyclohexylalanine (Cha); norleucine (Nle); naphthylalanine (Nal); 2-chlorophenylalanine (Ocf); 3-chlorophenylalanine (Mcf); 4 chlorophenylalanine (Pcf); 2 fluorophenylalanine (Off); 3 fluorophenylalanine (Mff); 4 fluorophenylalanine (Pff); 2-bromophenylalanine (Obf); 3-bromophenylalanine (Mbf); 4-bromophenylalanine (Pbf); 2-methylphenylalanine (Omf); 3-methylphenylalanine (Mmf); 4-methylphenylalanine (Pmf); 2-nitrophenylalanine (Onf); 3-nitrophenylalanine (Mnf); 4-nitrophenylalanine (Pnf); 2-cyanophenylalanine (Ocf); 3-cyanophenylalanine (Mcf); 4-cyanophenylalanine (Pcf); 2-trifluoromethylphenylalanine (Otf); 3-trifluoromethylphenylalanine (Mtf); 4-trifluoromethylphenylalanine (Ptf); 4-aminophenylalanine (Paf); 4-iodophenylalanine (Pif); 4-aminomethylphenylalanine (Pamf); 2,4-dichlorophenylalanine (Opef); 3,4-dichlorophenylalanine (Mpcf); 2,4-difluorophenylalanine (Opff); 3,4-difluorophenylalanine (Mpff); pyrid-2-ylalanine (2pAla); pyrid-3-ylalanine (3pAla); pyrid-4-ylalanine (4pAla); naphth-1-ylalanine (1nAla); naphth-2-ylalanine (2nAla); thiazolylalanine (taAla); benzothienylalanine (bAla); thienylalanine (tAla); furylalanine (fAla); homophenylalanine (hPhe); homotyrosine (hTyr); homotryptophan (hTrp); pentafluorophenylalanine (5ff); styrylkalanine (sAla); authrylalanine (aAla); 3,3-diphenylalanine (Dfa); 3-amino-5-phenypentanoic acid (Afp); penicillamine (Pen); 1,2,3,4-tetrahydroisoquinoline-3-carboxylic acid (Tic); β 2-thienylalanine (Thi); methionine sulfoxide (Mso); N(w)-nitroarginine (nArg); homolysine (hLys); phosphonomethylphenylalanine (pmPhe); phosphoserine (pSer); phosphothreonine (pThr); homoaspartic acid (hAsp); homoglutamic acid (hGlu); 1-aminocyclopent-(2 or 3)-ene-4 carboxylic acid; pipecolic acid (PA), azetidine-3-carboxylic acid (ACA); 1-aminocyclopentane-3-carboxylic acid; allylglycine (aOly); propargylglycine (pgGly); homoalanine (hAla); norvaline (nVal); homoleucine (hLeu), homovaline (hVal); homoisoleucine (hIle); homoarginine (hArg); N acetyl lysine (AcLys); 2,4 diaminobutyric acid (Dbu); 2,3-diaminobutyric acid (Dab); N-methylvaline (MeVal); homocysteine (hCys); homoserine (hSer); hydroxyproline (Hyp) and homoproline (hPro). Additional non-encoded amino acids of which the polypeptides described herein may be comprised will be apparent to those of skill in the art (see, e.g., the various amino acids provided in Fasman, 1989, CRC Practical Handbook of Biochemistry and Molecular Biology, CRC Press, Boca Raton, Fla., at pp. 3-70 and the references cited therein, all of which are incorporated by reference). These amino acids may be in either the L or D configuration.

Those of skill in the art will recognize that amino acids or residues bearing side chain protecting groups may also comprise the polypeptides described herein. Non-limiting examples of such protected amino acids, which in this case belong to the aromatic category, include (protecting groups listed in parentheses), but are not limited to: Arg(tos), Cys(methylbenzyl), Cys (nitropyridinesulfenyl), Glu(δ-benzylester), Gln(xanthyl), Asn(N-δ-xanthyl), His(bom), His (benzyl), His(tos), Lys(fmoc), Lys(tos), Ser(O-benzyl), Thr (O-benzyl) and Tyr(O-benzyl).

Non-encoding amino acids that are conformationally constrained of which the polypeptides described herein may be composed include, but are not limited to, N methyl amino acids (L configuration); 1 aminocyclopent-(2 or 3)-ene-4-carboxylic acid; pipecolic acid; azetidine-3-carboxylic acid; homoproline (hPro); and 1 aminocyclopentane-3-carboxylic acid.

As described above the various modifications introduced into the naturally occurring polypeptide to generate an engineered transaminase enzyme can be targeted to a specific property of the enzyme.

In another aspect, the present disclosure provides polynucleotides encoding the improved transaminase polypeptides. The polynucleotides may be operatively linked to one or more heterologous regulatory sequences that control gene expression to create a recombinant polynucleotide capable of expressing the transaminase polypeptide. Expression constructs containing a heterologous polynucleotide encoding the engineered transaminase can be introduced into appropriate host cells to express the corresponding transaminase polypeptide.

Because of the knowledge of the codons corresponding to the various amino acids, availability of a protein sequence provides a description of all the polynucleotides capable of encoding the subject. The degeneracy of the genetic code, where the same amino acids are encoded by alternative or synonymous codons allows an extremely large number of nucleic acids to be made, all of which encode the improved transaminase polypeptides disclosed herein. Thus, having identified a particular amino acid sequence, those skilled in the art could make any number of different nucleic acids by simply modifying the sequence of one or more codons in a way which does not change the amino acid sequence of the protein. In this regard, the present disclosure specifically contemplates each and every possible variation of polynucleotides that could be made by selecting combinations based on the possible codon choices, and all such variations are to be considered specifically disclosed for any polypeptide disclosed herein.

In some embodiments, the polynucleotides can be selected and/or engineered to comprise codons that are preferably selected to fit the host cell in which the protein is being produced. For example, preferred codons used in bacteria are used to express the gene in bacteria; preferred codons used in yeast are used for expression in yeast; and preferred codons used in mammals are used for expression in mammalian cells. Since not all codons need to be replaced to optimize the codon usage of the transaminases (e.g., because the natural sequence can have preferred codons and because use of preferred codons may not be required for all amino acid residues), codon optimized polynucleotides encoding the transaminase polypeptides may contain preferred codons at about 40%, 50%, 60%, 70%, 80%, or greater than 90% of codon positions of the full length coding region.

Solid Support

Described herein are immobilized transaminases comprising a transaminase that is physically attached to a solid support. Support materials can comprise a wide range of material, either biological, nonbiological, organic, inorganic, or a combination of any of these. For example, the support material may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic acid, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonate, or combinations thereof. Support materials can be planar crystalline support materials such as silica based support materials (e.g. glass, quartz, or the like), or crystalline support materials used in, e.g., the semiconductor and microprocessor industries, such as silicon, gallium arsenide and the like. Silica aerogels can also be used as support materials, and can be prepared by methods known in the art. Aerogel support materials may be used as free standing substrates or as a surface coating for another support material.

A support material can take any form or shape and typically is a plate, slide, bead, pellet, disk, particle, strand, precipitate, membrane, optionally porous gel, sheets, tube, sphere, container, capillary, pad, slice, film, chip, multiwell plate or dish, optical fiber, etc. Although typically the support material takes an inanimate form, for some attachment peptide applications such as flow cytometry or in situ hybridization, it can be any form that is rigid or semi-rigid. The support material may contain raised or depressed regions on which a capture probe is located. The surface of the support material can be etched using well known techniques to provide for desired surface features, for example trenches, v-grooves, mesa structures, or the like.

Surfaces on the support material can be composed of the same material as the interior part of the support or can be made from a different material, and can be coupled to the interior support material by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed support materials. In one embodiment, the surface is optically transparent and can have surface Si—OH functionalities, such as those found on silica surfaces.

Glass or plastic microscope slides have commonly been used as solid matrix supports for microarray analysis. Opaque matrix-coating materials used to produce microarrays include nylon, PVDF (polyvinylidene fluoride) and nitrocellulose. Nitrocellulose, a traditional polymer substrate in use for more than 50 years, can be used for microarray attachment applications. (E.g., Tonkinson and Stillman, Frontiers in Bioscience 7:c1-12, 2002.) Opaque nitrocellulose has been extensively used to immobilize proteins and nucleic acids for biomolecular analysis. Nitrocellulose immobilizes molecules of interest in near quantitative fashion and allows for short and long term storage. Nitrocellulose also allows for solution phase target species to efficiently bind to immobilized entities.

A solid support may be of any suitable composition to which the attachment molecule may be applied. It may be pretreated or functionalized prior to application of the attachment/molecule peptide to facilitate binding of the attachment molecules, or for any other desired purpose, such as fostering conditions favorable for the activity or any other desired property of the entity or avoiding undesired interactions with other entities. Many such surface treatments and/or functionalizations are known in the art and selection of a suitable treatment and/or functionalization will depend upon the identity and characteristics of the attachment molecule/peptide and entity and upon the attendant conditions and desired activity.

With regard to the immobilized transaminases described herein the solid support is a resin. Resins can be made from any suitable composition including, but not limited to, polymethacrylate and styrene/DVB copolymer. Such resins can include functional groups and facilitate the convalent bonding of the recombinant transaminase to the resin. Suitable functional groups include, but are not limited to, epoxide and amino epoxide. Additionally, other functional groups such as octadecyl and resins that include a porous structure facilitate in generating hydrophobic interactions with the recombinant transaminase.

In certain embodiments of the immobilized transaminases described herein, the resin comprises methacrylate. Examples of suitable resins include, but are not limited to, DIAION HP2MG (Mitsubishi).

The following table sets out a preferred resin that can be used in connection with the immobilized transaminases described herein:

TABLE 1

| Resin Name (Mitsubishi) | Resin Composition | Resin Functional Group |
|---|---|---|
| DIAION HP2MG | Monomer and crosslinker are methacrylate | none |

In certain embodiments of the immobilized transaminase described herein, the immobilized tranaminase includes a resin that is physically attached to the transaminase. Suitable resins comprise methacrylates with no aromatic compounds or other functional groups. Examples include, but are not limited to, DIAION HP2MG (Mitsubishi).

In still other embodiments of the immobilized described herein, the immobilized transaminase is comprised of the transaminase SEQ ID NO: 1 physically attached to the resin DIAION HP2MG (Mitsubishi). In still other embodiments of the immobilized described herein, the immobilized transaminase is comprised of the transaminase SEQ ID NO: 1 physically attached to the resin DIAION HP2MG (Mitsubishi) via hydrophilic interactions.

Process for Making the Immobilized Transaminase

Also described herein are processes for making the immobilized transaminase. In certain embodiments of the processes for making the immobilized transaminases described herein, the process begins with making an enzyme solution by dissolving the enzyme in water or a buffered solution. The transaminase polypeptide may use pyridoxal phosphate (PLP) as a coenzyme, which may be bound to the enzyme when prepared, e.g., as provided by the host cell in which the polypeptide is expressed. In some embodiments, PLP, PLP analogs, or precursors to PLP can be added to the media of host cells during expression of the transaminase polypeptide. In some embodiments of the processes, PLP or PLP analogs can be added to a reaction to provide the coenzyme required for enzyme activity. The amount of PLP sufficient for enzyme activity can be determined by one of skill in the art.

In some embodiments of the processes for making the immobilized transaminase, the transaminase solution can comprise a pH of about 5.0 to about 9.0. In some embodiments, the reaction condition for the process is a pH of about 7.5 to about 8.5. In still other embodiments, the reaction condition for the process is a pH of about 7.

Additionally, a solvent can be added to the enzyme solution. Suitable organic solvents that can be used in the processes described herein include any organic solvent commonly known in the art such as, methanol, ethanol, THF, DMSO, toluene, isopropylacetate, hexanes, isopropanol, propanol, bezene, acetone, xylene, methylethyl ketone, ether and ethyl acetate and mixtures thereof. In certain examples of the processes described herein the organic solvent is isopropanol.

The process further comprises contacting or incubating the transaminase with a resin. This can be done by adding the resin to the solution. The solution is then agitated for a length of time, such as overnight. Alternatively, the enzyme solution can be contacted with the resin either in batch or continuous mode. For example, resin can be packed into a column and the enzyme solution can then be passed through the column.

In some embodiments, the reaction condition for carrying out the process can comprise a temperature of about 5° C. to about 70° C. In some embodiments, the reaction condition is a temperature of about 25° C. (room temperature).

If the process is done in solution, once the reaction if complete the immobilized transaminase is filtered and rinsed. After the immobilized enzyme is rinsed with water or other solvents, in certain embodiments of the processes described herein, the preparation is dried before it is used in a 100% organic solvent system. The immobilized enzyme can be dried under vacuum with a nitrogen sweep to remove water from the outer surface of the immobilized enzyme resin. The immobilized preparation can be stirred while drying to allow for even moisture content throughout the immobilized enzyme bed and to prevent over- or under-drying any portion of the immobilized enzyme preparation. The immobilized preparation can also be dried by washing with organic solvents. Over-drying can result in loss of activity as water is stripped away from the enzyme molecule attached to the resin. Under-drying can result in insufficient mass transfer in an organic solvent system to affect the transamination of the desired substrate.

If the process is done in batch or continuous mode, washes are done continuously with the resin packed in the column. Further reactions are started using the packed column reactor.

Processes for Using the Immobilized Transaminase

The immobilized transaminases described herein can be used to transfer an amino group ($NH_2$) and a hydrogen atom from a primary amine to an acceptor carbonyl compound, converting the amine donor into its corresponding carbonyl compound and the acceptor into its corresponding primary amine Such a process comprises contacting the acceptor carbonyl compound with an immobilized transaminase described herein in presence of an amino group donor in a suitable organic solvent under suitable reaction conditions wherein the acceptor carbonyl compound is converted to its corresponding primary amine.

In some embodiments, the immobilized transaminases can be used in a process for preparing a compound of structural formula (I):

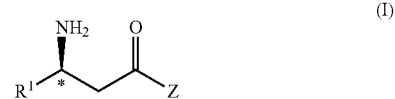

(I)

having the indicated stereochemical configuration at the stereogenic center marked with an *; in an enantiomeric excess of at least 70% over the opposite enantiomer, wherein Z is $OR^2$ or $NR^2R^3$;

$R^1$ is $C_{1-8}$ alkyl, aryl, heteroaryl, aryl-$C_{1-2}$ alkyl, or heteroaryl-$C_{1-2}$ alkyl;

$R^2$ and $R^3$ are each independently hydrogen, $C_{1-8}$ alkyl, aryl, or aryl-$C_{1-2}$ alkyl; or $R^2$ and $R^3$ together with the nitrogen atom to which they are attached form a 4- to 7-membered heterocyclic ring system optionally containing an additional heteroatom selected from O, S, NH, and $NC_{0-4}$ alkyl, the heterocyclic ring being unsubstituted or substituted with one to three substituents independently selected from oxo, hydroxy, halogen, $C_{1-4}$ alkoxy, and $C_{1-4}$ alkyl, wherein alkyl and alkoxy are unsubstituted or substituted with one to five fluorines; and the heterocyclic ring system being optionally fused with a 5- to 6-membered saturated or aromatic carbocyclic ring system or a 5- to 6-membered saturated or aromatic heterocyclic ring system containing one to two heteroatoms selected from O, S, and $NC_{0-4}$ alkyl, the fused ring system being unsubstituted or substituted with one to two substituents selected from hydroxy, amino, fluorine, $C_{1-4}$ alkyl, $C_{1-4}$ alkoxy, and trifluoromethyl. In these embodiments, the process comprises the step of contacting a prochiral ketone of structural formula (II):

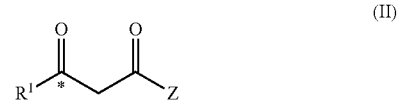

(II)

with an immobilized transaminase polypeptide in the presence of an amino group donor in a suitable organic solvent under suitable reaction conditions for the conversion of the compound of formula (II) to the compound of formula (I).

In some embodiments of the process, the $R^1$ of formula (II) is benzyl, wherein the phenyl group of benzyl is unsubstituted or substituted with one to three substituents selected from the group consisting of fluorine, trifluoromethyl, and trifluoromethoxy.

In some embodiments of the process, the Z of formula (II) is $NR^2R^3$.

In some embodiments of the process, the $NR^2R^3$ of formula (II) is a heterocycle of the structural formula (III):

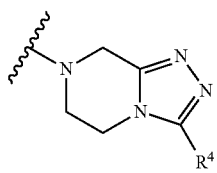

(III)

wherein $R^4$ is hydrogen or $C_{1-4}$ alkyl which is unsubstituted or substituted with one to five fluorines.

In some embodiments, the immobilized transaminases can be used in a process for preparing a compound of structural formula (1):

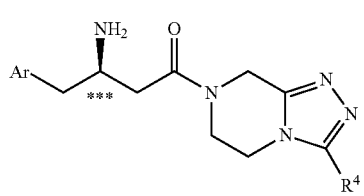

(1)

having the (R)-configuration at the stereogenic center marked with an ***, in an enantiomeric excess of at least 70% over the enantiomer having the opposite (S)-configuration; wherein Ar is phenyl which is unsubstituted or substituted with one to five substituents independently selected from the group consisting of fluorine, trifluoromethyl, and trifluoromethoxy; and $R^4$ is hydrogen or $C_{1-4}$ alkyl unsubstituted or substituted with one to five fluorines. In such embodiments, the process comprises the step of contacting a prochiral ketone of structural formula (2):

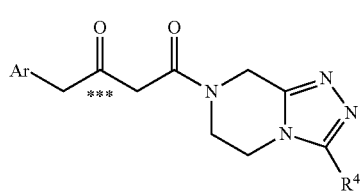

(2)

with an immobilized transaminase polypeptide disclosed herein in the presence of an amino group donor in a suitable organic solvent under suitable reaction conditions for the conversion of the compound of formula (2) to the compound of formula (1).

In some embodiments of the process, the Ar of formula (2) is 2,5-difluorophenyl or 2,4,5-trifluorophenyl, and $R^4$ is trifluoromethyl.

In some embodiments of the process, the Ar of formula (2) is 2,4,5-trifluorophenyl.

In some embodiments, the transaminases can be used in a process for preparing a compound of formula (1a), (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, in enantiomeric excess:

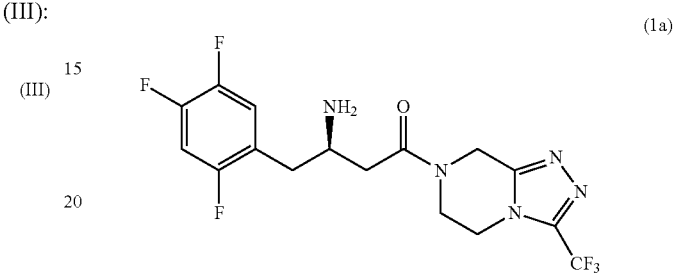

(1a)

In these embodiments, the process comprises the step of contacting a prochiral ketone of structural formula (2a), 4-oxo-4-[3-(trifluoromethyl)-5,6-dihydro[1,2,4]triazolo[4,3-a]pyrazin-7(8H)-yl]-1-(2,4,5-trifluorophenyl)butan-2-one):

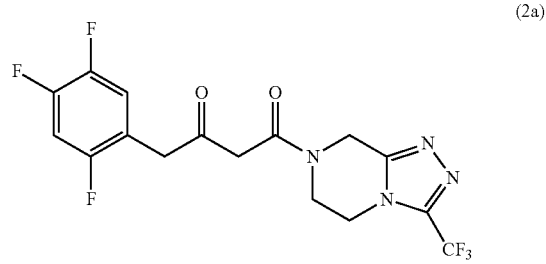 [SMILES: O=C(CC(=O)N1CCn2c(nnc2C(F)(F)F)C1)Cc1cc(F)c(F)cc1F]

(2a)

with an immobilized transaminase described herein in the presence of an amino group donor in a suitable organic solvent under suitable reaction conditions for the conversion of the compound of formula (2a) to the compound of formula (1a).

In some embodiments of the processes above, the compound of formula (I), the compound of formula (1) or the compound of formula (1a) is produced in at least 70%, 80%, 90%, 91%, 92%, 93%, 94%, 95%, 96%, 97%, 98%, 99% or more enantiomeric excess.

In some embodiments of the processes, the compound of formula (I), the compound of formula (1) or the compound of formula (1a) is produced in at least 99% enantiomeric excess.

The compound of formula (II), the compound of formula (2), and the compound of formula (2a), along with their syntheses, are described in, among others, U.S. Pat. Nos. 7,326,708 and 7,468,459, the disclosures of which are incorporated herein by reference in their entirety.

In some embodiments, the process of using the immobilized transaminases described herein comprises the steps of: 1) dissolving 4-oxo-4-[3-(trifluoromethyl)-5,6-dihydro[1,2,4]triazolo[4,3-a]pyrazin-7(8H)-yl]-1-(2,4,5-trifluorophenyl)

butan-2-one in an organic solvent; 2) contacting 4-oxo-4-[3-(trifluoromethyl)-5,6-dihydro[1,2,4]triazolo[4,3-a]pyrazin-7(8H)-yl]-1-(2,4,5-trifluorophenyl)butan-2-one with an immobilized transaminase described herein in the presence of an amino group.

Described herein are immobilized transaminases comprising a recombinant transaminase physically attached to a resin, wherein the transaminase is stable in organic solvents. Suitable organic solvents that can be used in the processes described herein include any organic solvent commonly known in the art such as, methanol, ethanol, THF, DMSO, toluene, isopropylacetate, hexanes, propanol, bezene, acetone, xylene, methylethyl ketone, ether and ethyl acetate and mixtures thereof. In certain examples of the processes described herein the organic solvent is isopropylacetate.

In certain embodiments the organic solvent is a non-water saturated solvent. In other embodiments the organic solvent is a water-saturated solvent. Water saturation may keep the immobilized enzyme at a constant water concentration and prevents further drying of the immobilized enzyme over the course of the reaction. This can allow for greater operational stability when the immobilized enzyme is isolated at the end of the reaction and reused for multiple batches. In certain examples of the processes described herein the organic solvent is water-saturated isopropylacetate.

In certain embodiments the solvent that the transaminase is stable in is a component of a solvent system. In certain embodiments of the processes for using the immobilized transaminases described herein, the solvent system is a 100% organic solvent system. In other embodiments the solvent system contains 50-60% organic solvents. Preferably, the solvent system contains 60-70% organic solvents. More preferably, the solvent system contains 70-80% organic solvents. More preferably, the solvent system contains 80-90% organic solvents. More preferably, the solvent system contains 90-100% organic solvents. In other embodiments the solvent system contains at least 50% organic solvents. In other embodiments the solvent system contains at least 55% organic solvents. Preferably, the solvent system contains at least 60% organic solvents. Preferably, the solvent system contains at least 65% organic solvents. More preferably, the solvent system contains at least 70% organic solvents. More preferably, the solvent system contains at least 75% organic solvents. More preferably, the solvent system contains at least 80% organic solvents. More preferably, the solvent system contains at least 85% organic solvents. More preferably, the solvent system contains at least 90% organic solvents. More preferably, the solvent system contains at least 95% organic solvents. More preferably, the solvent system contains at least 100% organic solvents. The solvent system can contain more than one organic solvent, wherein the immobilized transaminase is stable in one or all of the organic solvents present in the solvent system.

As discussed above, the amino group donor used in the process can be a chiral amine or an achiral amine. An achiral amino group donor has the advantage of not being limited in its reaction to a specific stereoisomer, thus requiring less of the amino group donor. Various suitable amino group donors can be used, including, by way of example and not limitation, isopropylamine (also referred to as 2-aminopropane), L, D or DL alanine, phenylalanine, glutamate, glutamine, leucine (or any other suitable α-amino acids), 3-aminobutyric acid (or any other suitable β-amino acids), and methylbenzylamine. In some embodiments, the amino group donor is isopropylamine. In some embodiments, other amino group donors may be used, including, among others, α-phenethylamine (also termed 1-phenylethanamine), and its enantiomers (S)-1-phenylethanamine and (R)-1-phenylethanamine, 2-amino-4-phenylbutane, glycine, L-glutamic acid, L-glutamate, monosodium glutamate, L-aspartic acid, L-lysine, L-ornithine, β-alanine, taurine, n-octylamine, cyclohexylamine, 1,4-butanediamine, 1,6-hexanediamine, 6-aminohexanoic acid, 4-aminobutyric acid, tyramine, and benzyl amine, 2-aminobutane, 2-amino-1-butanol, 1-amino-1-phenylethane, 1-amino-1-(2-methoxy-5-fluorophenyl)ethane, 1-amino-1-phenylpropane, 1-amino-1-(4-hydroxyphenyl)propane, 1-amino-1-(4-bromophenyl)propane, 1-amino-1-(4-nitrophenyl)propane, 1-phenyl-2-aminopropane, 1-(3-trifluoromethylphenyl)-2-aminopropane, 2-aminopropanol, 1-amino-1-phenylbutane, 1-phenyl-2-aminobutane, 1-(2,5-dimethoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, 3-methylcyclohexylamine, 1-aminotetralin, 2-aminotetralin, 2-amino-5-methoxytetralin, and 1-aminoindan, including both (R) and (S) single isomers where possible and including all possible salts of the amines. In certain examples of the processes described herein the amino donor is isopropylamine.

In certain examples of the processes described herein the immobilized transaminase is the transaminase SEQ ID NO: 1 physically attached to the resin DIAION HP2MG (Mitsubishi). In certain examples of the processes described herein the immobilized transaminase is the transaminase SEQ ID NO: 1 physically attached to the resin DIAION HP2MG (Mitsubishi) via hydrophilic interactions.

In some embodiments of the processes described above, the immobilized transaminases described herein can be recycled, wherein once the immobilized transaminases are filtered off once the reaction is complete and used in subsequent reactions. Thus certain processes described herein can further comprise the step of filtering off the immobilized transaminase and to be used in subsequent reactions.

In some embodiments of the processes above, a step in the process can further comprise removal of the carbonyl by-product formed from the amino group donor when the amino group is transferred to the amino group acceptor. Such removal in situ can reduce the rate of the reverse reaction such that the forward reaction dominates and more substrate is then converted to product.

Removal of the carbonyl by-product can be carried out in a number of ways. Where the amino group donor is an amino acid, such as alanine, the carbonyl by product, a keto acid, can be removed by reaction with peroxide (see, e.g., US 2008/0213845, incorporated herein by reference). Peroxides which can be used include, among others, hydrogen peroxide; peroxyacids (peracids) such as peracetic acid ($CH_3CO_3H$), trifluoroperacetic acid and metachloroperoxybenzoic acid; organic peroxides such as t-butyl peroxide (($CH_3)_3COOH$), or other selective oxidants such as tetrapropylammonium perruthenate, $MnO_2$, $KMnO_4$, ruthenium tetroxide and related compounds. Alternatively, pyruvate removal can be achieved via its reduction to lactate by employing lactate dehydrogenase to shift equilibrium to the product amine (see, e.g., Koszelewski et al., 2008, Adv. Syn. Catal. 350: 2761-2766). Pyruvate removal can also be achieved via its decarboxylation to carbon dioxide acetaldehyde by employing pyruvate decarboxylase (see, e.g., Hohne et al., 2008, Chem BioChem 9: 363-365).

In some embodiments, where the choice of the amino group donor results in a carbonyl by-product that has a vapor pressure higher than water (e.g., a low boiling co-product such as a volatile organic carbonyl compound), the carbonyl by-product can be removed by sparging the reaction solution with a non-reactive gas or by applying a vacuum to lower the reaction pressure and removing the carbonyl by-product present in the gas phase. A non-reactive gas is any gas that does not react with the reaction components. Various non-reactive gases include nitrogen and noble gases (e.g., inert gases). In some embodiments, the non-reactive gas is nitrogen gas.

In some embodiments, the amino acid donor used in the process is isopropylamine, which forms the carbonyl by-product acetone upon transfer of the amino group to the amino group acceptor. The acetone can be removed by sparging with nitrogen gas or applying a vacuum to the reaction solution and removing the acetone from the gas phase by an acetone trap, such as a condenser or other cold trap. Alternatively, the acetone can be removed by reduction to isopropanol using a ketoreductase.

In some embodiments of the processes above where the carbonyl by-product is removed, the corresponding amino group donor can be added during the transamination reaction to replenish the amino group donor and/or maintain the pH of the reaction. Replenishing the amino group donor also shifts the equilibrium towards product formation, thereby increasing the conversion of substrate to product. Thus, in some embodiments wherein the amino group donor is isopropylamine and the acetone product is removed in situ, isopropylamine can be added to the solution to replenish the amino group donor lost during the acetone removal. Alternatively, in embodiments where an amino acid is used as amino group donor, the keto acid carbonyl by-product can be recycled back to the amino acid by reaction with ammonia and NADH using an appropriate amino acid dehydrogenase enzyme, thereby replenishing the amino group donor.

The processes of using the immobilized transaminases described herein include batch process and continuous process. Continuous processes include processes wherein the ketone substrate is continuously contacting the immobilized transaminase and wherein the product is continuously being collected. Examples include wherein the immobilized transaminase is packed in a column and a solution of the ketone substrate is passed through the column. Thus the ketone is continuously contacting the immobilized resin and the product is collected after is has passed through the column.

In some embodiments, the process for converting ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprises dissolving the ketoamide substrate 4-oxo-4-[3-(trifluoromethyl)-5,6-dihydro[1,2,4]triazolo[4,3-a]pyrazin-7(8H)-yl]-1-(2,4,5-trifluorophenyl)butan-2-one to product (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in isopropylacetate; contacting the ketoamide substrate with an immobilized transaminase described herein under reaction conditions of a temperature of 30 to 70° C. in presence of isopropylamine of from about 1 M to about 4 M, wherein at least 80%, 85%, 90%, 92%, 94%, 96%, or 98% or more of the ketoamide substrate is converted to product in 24 hrs. In some embodiments, the immobilized transaminase capable of carrying out the foregoing reaction comprises an amino acid sequence corresponding to SEQ ID NO: 1 physically attached to a resin comprising DIAION HP2MG (Mitsubishi).

In some embodiments, the processes above can further comprise the step of isolating the compound of structural formula (I), the compound of structural formula (1), or the compound of structural formula (1a) from the reaction solvent.

In some embodiments, the processes above can further comprise a step of converting the compound of structural formula (1) or the compound of structural formula (1a) into a pharmaceutically acceptable salt by contacting the compound with a pharmaceutically acceptable acid in a suitable reaction solvent. In some embodiments, the pharmaceutically acceptable acid is phosphoric acid and the pharmaceutically acceptable salt is the dihydrogenphosphate salt. In some embodiments, the salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine is the phosphate monohydrate salt, having the following chemical formula:

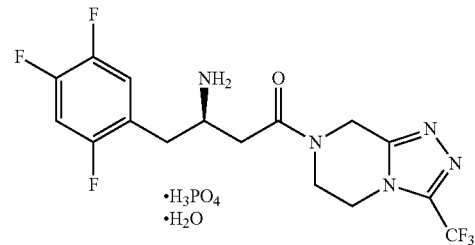 [SMILES: N[C@@H](CC(=O)N1CCn2c(nnc2C(F)(F)F)C1)Cc1cc(F)c(F)cc1F]

In some embodiments, in a process for the preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate (1:1) monohydrate, the improvement in the process comprises a step of converting the compound of formula (1a) to the compound of formula (2a) with an immobilized transaminase described herein in presence of an amino group donor in a suitable organic solvent under suitable reaction conditions, wherein the compound of formula (1a) is (1a)

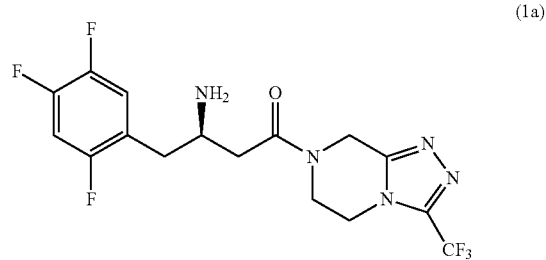

and the compound of formula (2a) is:

(2a)

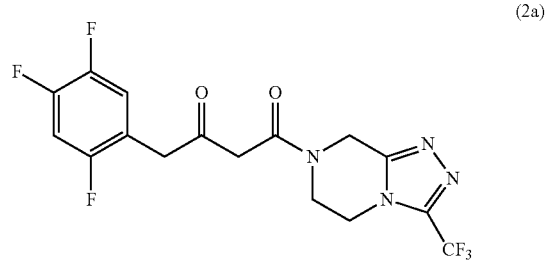 [SMILES: O=C(CC(=O)N1CCn2c(nnc2C(F)(F)F)C1)Cc1cc(F)c(F)cc1F]

In some embodiments of the preparation of the phosphate monohydrate salt, the amino donor is isopropylamine.

Methods for preparing various salts are described in U.S. Pat. Nos. 7,326,708 and 7,468,459, each of which is hereby incorporated by reference herein.

Example

Preparation of Enzyme Solution

TABLE 2

| Example | Resin | Composition |
|---------|-------|-------------|
| 1 | DIAION HP2MG (Mitsubishi) | methacrylate |

In a 50 mL round bottom flask equipped with a magnetic bar is placed 10 mL of 100 mM aqueous phosphate buffer solution (pH-7). 2.0 g of lyophilized enzyme (200 g/L) is added in one portion and stirred at room temperature for 1 hour. PLP (80 mg, 8 g/L) is then added in one portion as well and stirred for 1 hour at room temperature.

In Column Immobilization

A column is charged with 4.1 g of wet Mitsubishi HP2MG Diaion® resin (ca. 50 wt %). The resulting "liquid volume" of the column is measured at 3.8 mL. 9.5 mL (2.5 volumes) of the above solution is pumped through the resin at room temperature in 3 hours with a syringe pump (flow rate of 53 μL/min) Pumping is then stopped, and the column is held at room temperature for 2 hours before a solution of wet IPAc (water saturated, 10 volumes, 38 mL) is pumped within 12 hours still at the same flow rate.

The column is then placed into a hot bath held at +60° C., and a solution of ketoamide (20 wt % in wet IPAc) containing 2 equivalents of isopropylamine is pumped through the column at a flow rate of 63 μL/min corresponding to a 1 h residence time. Conversion is calculated at 45% after 2 bed volumes (7.6 mL) have been pumped with an e.e>99.5%. Conversion increase to 70% with a residence time of 2 hours (flow rate of 32 μL/min), and 85% at 4 hours residence time (flow rate of 16 μL/min). The immobilized enzyme exhibits a faster conversion time, up to 4.5 times faster, as compared to immobilized resins described in PCT/US12/042,853.

Resin performance was then evaluated vs. the lyophilized enzyme preparation in the following transamination:

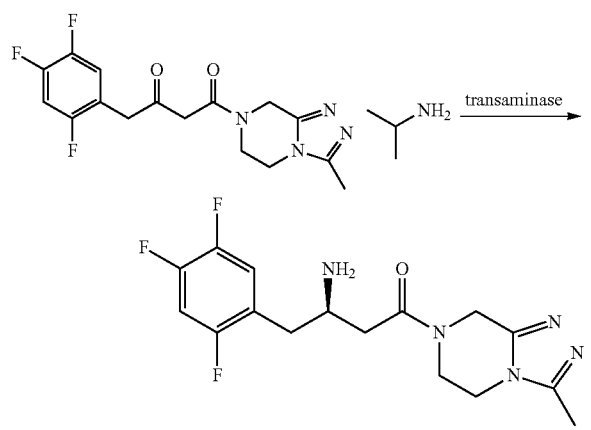

The immobilized tranaminase preparations exhibited good specific activity compared to the lyophilized enzyme.

Sequence Listing

In some embodiments of the present invention SEQ ID NO: 1 may be encoded be SEQ ID NO: 2. SEQ ID NO: 1 and SEQ ID NO: 2 are further described in the table below:

| Number | Sequence |
|--------|----------|
| SEQ ID NO: 1 | Met Ala Phe Ser Ala Asp Thr Pro Glu Ile Val Tyr Thr His Asp Thr Gly Leu Asp Tyr Ile Thr Tyr Ser Asp Tyr Glu Leu Asp Pro Ala Asn Pro Leu Ala Gly Gly Ala Ala Trp Ile Gly Gly Ala Phe Val Pro Pro Ser Glu Ala Arg Ile Pro Ile Phe Asp Gln Gly Phe Tyr Thr Ser Asp Ala Thr Tyr Thr Thr Phe His Val Trp Asn Gly Asn Ala Phe Arg Leu Gly Asp His Ile Glu Arg Leu Phe Ser Asn Ala Glu Ser Ile Arg Leu Ile Pro Pro Leu Thr Gln Asp Glu Val Lys Glu Ile Ala Leu Glu Leu Val Ala Lys Thr Glu Leu Arg Glu Ala Met Val Thr Val Thr Ile Thr Arg Gly Tyr Ser Ser Thr Pro Phe Glu Arg Asp Ile Thr Lys His Arg Pro Gln Val Tyr Met Phe Ala Ser Pro Tyr Leu Gln Ile Val Pro Phe Asp Arg Ile Arg Asp Gly Val His Leu Met Val Ala Gln Ser Val Arg Arg Thr Pro Arg Ser Ser Ile Asp Pro Gln Val Lys Asn Phe Gln Trp Gly Asp Leu Ile Arg Ala Ile Gln Glu Thr His Asp Arg Gly Phe Glu Leu Pro Leu Leu Leu Asp Gly Asp Asn Leu Leu Ala Glu Gly Pro Gly Phe Asn Val Val Val Ile Lys Asp Gly Val Val Arg Ser Pro Gly Arg Ala Ala Leu Pro Gly Ile Thr Arg Lys Thr Val Leu Glu Ile Ala Glu Ser Leu Gly His Glu Ala Ile Leu Ala Asp Ile Thr Pro Ala Glu Leu Tyr Asp Ala Asp Glu Val Leu Gly Cys Ser Thr Gly Gly Gly Val Trp Pro Phe Val Ser Val Asp Gly Asn Ser Ile Ser Asp Gly Val Pro Gly Pro Val Thr Gln Ser Ile Ile Arg Arg Tyr Trp Glu Leu Asn Val Glu Pro Ser Ser Leu Leu Thr Pro Val Gln Tyr |
| SEQ ID NO: 2 | atggcgttct cagcggacac ccctgaaatc gtttacaccc acgacaccgg tctggactat atcacctact ctgactacga actggacccg gctaacccgc tggctggtgg tgctgcttgg tgcggaggtg ctttcgttcc gccgtcggaa gctcgtatcc cgatcttcga ccagggtttt tatacttctg acgctaccta caccaccttc cacgtttgga acggtaacgc tttccgtctg ggggaccaca tcgaacgtct gttctctaat gcggaatcta ttcgtttgat cccgccgctg acccaggacg aagttaaaga ggtggctctg gaactggttg ctaaaaccga actgcgtgaa gcgatggtta ccgttacgat cacccgtggt tactcttcta ccccattcga gcgtgacatc accaaacatc gtccgcaggt ttacatgttc gctagcccgt acaaacagat cgtaccgttt gaccgcatcc gggacggtgt tcacctgatg gttgctcagt cagttcgtcg tacaccgcgt agctctatcg acccgcaggt taaaaacttc cagtggggtg acctgatccg tgcaattcag gaaacccacg atcgtggttt cgagttgccg ctgctgctgg acggggacaa cctgctggct gaaggtccgg gtttcaacgt tgttgttatc aaagacggtg ttgttcgttc tccgggtcgt gctgctctgc cgggtatcac ccgtaaaacc gttctggaaa tcgctgaatc tctgggtcac gaagctatcc tggctgacgt taccccggct gaactgtacg acgctgacga agttctgggt tgctcaaccg gtggtggtgt ttggccgttc gtttctgttg acggtaactc tatctctgac ggtgttccgg gtccggttac ccagtctatc atccgtcgtt actgggaact gaacgttgaa ccttcttctc tgctgacccc ggtacagtac |

What is claimed is:

1. A resin comprising an immobilized transaminase polypeptide, wherein the transaminase polypeptide comprises the amino acid sequence of SEQ ID NO: 1, wherein the resin comprises methacrylate, and wherein the transaminase polypeptide is attached to the resin.

2. The resin of claim 1, wherein the transaminase is attached to the resin by hydrophilic interactions.

3. The resin of claim 1, wherein the resin comprises DIAION HP2MG.

4. The resin of claim 3, wherein the transaminase is stable in a solvent system that comprises at least 90% organic solvent.

5. The resin of claim 3, wherein the transaminase is stable in a solvent system that comprises at least 95% organic solvent.

6. The resin of claim 2, wherein the resin comprises methacrylate with no functional groups.

7. The resin of claim 2, wherein the resin comprises methacrylate with no aromatic groups.

8. A resin comprising an immobilized transaminase polypeptide, wherein the transaminase polypeptide comprises the amino acid sequence of SEQ ID NO: 1, wherein the resin comprises DIAION HP2MG, and wherein the transaminase polypeptide is physically attached to the resin via hydrophilic interactions.

9. A process for making (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine comprising the steps of:
1) dissolving 4-oxo-4-[3-(trifluoromethyl)-5,6-dihydro[1,2,4]triazolo[4,3-a]pyrazin-7(8H)-yl]-1-(2,4,5-trifluorophenyl)butan-2-one in an organic solvent; and
2) contacting the 4-oxo-4-[3-(trifluoromethyl)-5,6-dihydro[1,2,4]triazolo[4,3-a]pyrazin-7(8-H)-yl]-1-(2,4,5-trifluorophenyl)butan-2-one with the resin comprising the immobilized transaminase of claim 1 and an amino group donor to thereby make (2R)-4-oxo-4-[3-(trifluoromethyl)-5,6-dihydro[1,2,4]triazolo[4,3-a]pyrazi-n-7(8H)-yl]-1-(2,4,5-trifluorophenyl)butan-2-amine.

10. The process of claim 9 wherein the immobilized transaminase is physically attached to the resin, and the resin is DIAION HP2MG.

11. A process of making a resin comprising an immobilized transaminase comprising the steps of:
1) incubating a solution of a transaminase polypeptide with a resin to form a resin comprising an immobilized transaminase polypeptide, wherein the transaminase polypeptide comprises the amino acid sequence of SEQ ID NO: 1, wherein the resin comprises methacrylate, and wherein the transaminase polypeptide is attached to the resin; and
2) filtering and rinsing the immobilized transaminase.

* * * * *

SEQUENCE LISTING

<160> NUMBER OF SEQ ID NOS: 2

<210> SEQ ID NO 1
<211> LENGTH: 330
<212> TYPE: PRT
<213> ORGANISM: Artificial Sequence
<220> FEATURE:
<223> OTHER INFORMATION: Engineered variant of Arthobacter transaminase

<400> SEQUENCE: 1

Met Ala Phe Ser Ala Asp Thr Pro Glu Ile Val Tyr Thr His Asp Thr
1               5                   10                  15

Gly Leu Asp Tyr Ile Thr Tyr Ser Asp Tyr Glu Leu Asp Pro Ala Asn
                20                  25                  30

Pro Leu Ala Gly Gly Ala Ala Trp Ile Gly Gly Ala Phe Val Pro Pro
            35                  40                  45

Ser Glu Ala Arg Ile Pro Ile Phe Asp Gln Gly Phe Tyr Thr Ser Asp
50                  55                  60

Ala Thr Tyr Thr Thr Phe His Val Trp Asn Gly Asn Ala Phe Arg Leu
65                  70                  75                  80

Gly Asp His Ile Glu Arg Leu Phe Ser Asn Ala Glu Ser Ile Arg Leu
                85                  90                  95

Ile Pro Pro Leu Thr Gln Asp Glu Val Lys Glu Ile Ala Leu Glu Leu
            100                 105                 110

Val Ala Lys Thr Glu Leu Arg Glu Ala Met Val Thr Val Thr Ile Thr
        115                 120                 125

Arg Gly Tyr Ser Ser Thr Pro Phe Glu Arg Asp Ile Thr Lys His Arg
130                 135                 140

Pro Gln Val Tyr Met Phe Ala Ser Pro Tyr Leu Gln Ile Val Pro Phe
145                 150                 155                 160

Asp Arg Ile Arg Asp Gly Val His Leu Met Val Ala Gln Ser Val Arg
                165                 170                 175

Arg Thr Pro Arg Ser Ser Ile Asp Pro Gln Val Lys Asn Phe Gln Trp
            180                 185                 190

Gly Asp Leu Ile Arg Ala Ile Gln Glu Thr His Asp Arg Gly Phe Glu
        195                 200                 205

Leu Pro Leu Leu Leu Asp Gly Asp Asn Leu Leu Ala Glu Gly Pro Gly
210                 215                 220

Phe Asn Val Val Val Ile Lys Asp Gly Val Val Arg Ser Pro Gly Arg
225                 230                 235                 240

Ala Ala Leu Pro Gly Ile Thr Arg Lys Thr Val Leu Glu Ile Ala Glu
                245                 250                 255

Ser Leu Gly His Glu Ala Ile Leu Ala Asp Ile Thr Pro Ala Glu Leu
            260                 265                 270

Tyr Asp Ala Asp Glu Val Leu Gly Cys Ser Thr Gly Gly Val Trp
        275                 280                 285

Pro Phe Val Ser Val Asp Gly Asn Ser Ile Ser Asp Gly Val Pro Gly
290                 295                 300

Pro Val Thr Gln Ser Ile Ile Arg Arg Tyr Trp Glu Leu Asn Val Glu
305                 310                 315                 320

Pro Ser Ser Leu Leu Thr Pro Val Gln Tyr
                325                 330

<210> SEQ ID NO 2
<211> LENGTH: 990
<212> TYPE: DNA

```
<213> ORGANISM: Artificial Sequence
<220> FEATURE:
<223> OTHER INFORMATION: Engineered transaminase variant

<400> SEQUENCE: 2
atggcgttct cagcggacac ccctgaaatc gtttacaccc acgacaccgg tctggactat      60
atcacctact ctgactacga actggacccg gctaacccgc tggctggtgg tgctgcttgg     120
tgcggaggtg ctttcgttcc gccgtcggaa gctcgtatcc cgatcttcga ccagggtttt     180
tatacttctg acgctaccta caccaccttc cacgtttgga acggtaacgc tttccgtctg     240
ggggaccaca tcgaacgtct gttctctaat gcggaatcta ttcgtttgat cccgccgctg     300
acccaggacg aagttaaaga ggtggctctg gaactggttg ctaaaaccga actgcgtgaa     360
gcgatggtta ccgttacgat cacccgtggt tactcttcta ccccattcga gcgtgacatc     420
accaaacatc gtccgcaggt ttacatgttc gctagcccgt acaaacagat cgtaccgttt     480
gaccgcatcc gggacggtgt tcacctgatg gttgctcagt cagttcgtcg tacaccgcgt     540
agctctatcg acccgcaggt taaaaacttc cagtggggtg acctgatccg tgcaattcag     600
gaaacccacg atcgtggttt cgagttgccg ctgctgctgg acggggacaa cctgctggct     660
gaaggtccgg gtttcaacgt tgttgttatc aaagacggtg ttgttcgttc tccgggtcgt     720
gctgctctgc cgggtatcac ccgtaaaacc gttctggaaa tcgctgaatc tctgggtcac     780
gaagctatcc tggctgacgt taccccggct gaactgtacg acgctgacga agttctgggt     840
tgctcaaccg gtggtggtgt ttggccgttc gtttctgttg acggtaactc tatctctgac     900
ggtgttccgg gtccggttac ccagtctatc atccgtcgtt actgggaact gaacgttgaa     960
ccttcttctc tgctgacccc ggtacagtac                                     990
```